United States Patent
Deurenberg et al.

(10) Patent No.: US 11,968,003 B2
(45) Date of Patent: Apr. 23, 2024

(54) CONNECTOR PROVIDING A CONNECTION THROUGH A FLEXIBLE BARRIER

(71) Applicant: PHILIPS IMAGE GUIDED THERAPY CORPORATION, San Digeo, CA (US)

(72) Inventors: Peter Hubertus Franciscus Deurenberg, Noord Brabant (NL); Alfons Wouter Groenland, Best (NL); Albert Hendrik Jan Immink, Eindhoven (NL); Andrew Mitchell, Noord Brabant (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 275 days.

(21) Appl. No.: 17/442,264

(22) PCT Filed: Mar. 26, 2020

(86) PCT No.: PCT/EP2020/058600
§ 371 (c)(1),
(2) Date: Sep. 23, 2021

(87) PCT Pub. No.: WO2020/193720
PCT Pub. Date: Oct. 1, 2020

(65) Prior Publication Data
US 2022/0166462 A1 May 26, 2022

(30) Foreign Application Priority Data
Mar. 26, 2019 (EP) .................................. 19165164

(51) Int. Cl.
*A61B 5/02* (2006.01)
*A61B 5/00* (2006.01)
(Continued)

(52) U.S. Cl.
CPC ......... *H04B 5/0031* (2013.01); *A61B 5/7475* (2013.01); *A61B 46/20* (2016.02); *H04B 5/0037* (2013.01); *A61B 2562/225* (2013.01)

(58) Field of Classification Search
None
See application file for complete search history.

(56) References Cited

U.S. PATENT DOCUMENTS 9,649,048 B2 * 5/2017 Cox .................... A61B 8/0841
10,426,468 B2 * 10/2019 Contini ............ A61B 17/07207
(Continued)

FOREIGN PATENT DOCUMENTS

| JP | 2000254141 A | 9/2000 |
| WO | 2015116111 A1 | 8/2015 |

OTHER PUBLICATIONS

International Search Report and Written Opinion of PCT/EP2020/058600, dated Jun. 9, 2020.

*Primary Examiner* — Tuan A Tran (57) ABSTRACT

The present invention relates to a connector for connection through a flexible barrier. The connector comprises at least a device pad and at least a landing pad. The device pad is arranged in close proximity to the landing pad for contactless connection through the flexible barrier to transmit and/or receive data and/or power between each other. The device pad and the landing pad are configured to attach and/or align to each other. Furthermore, a system for connection through a flexible barrier, an according method, computer program element and computer readable medium are provided.

20 Claims, 8 Drawing Sheets

(51) Int. Cl.
  *A61B 5/0215* (2006.01)
  *A61B 46/20* (2016.01)
  *H04B 5/00* (2006.01)

(56) References Cited

U.S. PATENT DOCUMENTS

| | | | |
|---|---|---|---|
| 10,675,442 B2 * | 6/2020 | Douglas | A61M 25/0147 |
| 10,814,102 B2 * | 10/2020 | Laby | A61B 34/20 |
| 11,369,274 B2 * | 6/2022 | Anderson | A61B 5/14552 |
| 11,529,070 B2 * | 12/2022 | Silverstein | A61B 5/283 |
| 11,607,150 B2 * | 3/2023 | Schweikert | A61B 5/282 |
| 11,607,284 B2 * | 3/2023 | Zemlok | B25J 5/00 |
| 11,717,644 B2 * | 8/2023 | Douglas | A61M 25/0147 604/95.01 |
| 2007/0290654 A1 | 12/2007 | Govari | |
| 2008/0147089 A1 | 6/2008 | Loh | |
| 2009/0234328 A1 | 9/2009 | Cox | |
| 2012/0062175 A1 | 3/2012 | Miller | |
| 2016/0331460 A1 | 11/2016 | Cheatham | |
| 2017/0111943 A1 | 4/2017 | Kersjes | |
| 2017/0194820 A1 | 7/2017 | Hall | |
| 2018/0021586 A9 | 1/2018 | Mashiach | |
| 2018/0168761 A1 | 6/2018 | Vargas | |
| 2018/0311473 A1 * | 11/2018 | Laby | A61B 34/30 |
| 2019/0282313 A1 | 9/2019 | Devengenzo | |

* cited by examiner

CONNECTOR PROVIDING A CONNECTION THROUGH A FLEXIBLE BARRIER

CROSS-REFERENCE TO PRIOR APPLICATIONS

This application is the U.S. National Phase application under 35 U.S.C. § 371 of International Application No. PCT/EP2020/058600, filed on Mar. 26, 2020, which claims the benefit of European Patent Application No. 19165164.5, filed on Mar. 26, 2019. These applications are hereby incorporated by reference herein.

FIELD OF THE INVENTION

The present invention relates to a connector for connection through a flexible barrier, a system comprising the connector and an interventional device, a method for connection through a flexible barrier, a computer program element and a computer readable medium.

BACKGROUND OF THE INVENTION

Image guided therapy (IGT) devices for coronary or peripheral interventions is usually provided with catheters inserted into arteries of the human body and directed to the proper location in the human body by the physician. Such interventions usually take place in an operation room, a laboratory room or similar room, in the following referred to as cathlab.

One of the biggest challenges of present cathlab workflows is probably managing the sterility barrier when using active devices such as intravascular ultrasound (IVUS) or functional measurements (FM) catheters for measuring flow and pressure. The sterility barrier provides the connection between a sterile catheter and a non-sterile patient interface module (PIM) at a patient table. The sterile barrier itself is usually a drape. All electrical equipment in the sterile zone needs to cross this drape. Thus, managing the cables of the electrical equipment during an operation procedure can be practically challenging.

Despite the limited interventional character of such intervention procedures where the catheters are inserted into the body through small incisions, there are stringent measures ensuring sterility of the procedure. These result in a drape which is a sterile sheet of plastic placed over the patient, with an opening at the entry site for the patient for appropriate catheter insertion. The drape also covers devices mounted at the (bedrail of the) patient table, including PIM devices.

With respect to the cathlab useflow, crossing the sterility barrier during interventions is one of the biggest challenges for the use flow and might result in non-obvious, sub-optimal procedures to ensure that a sterile physician does not touch the non-sterile PIM when connecting the catheter. Often a non-sterile nurse makes this connection, because the PIM is mounted on the opposite side of the patient table in order to be out of the way. The handover of the sterile connector from the sterile physician to the non-sterile nurse can be challenging, because they must not touch each other. In practice, the physician often throws the connector towards the non-sterile nurse where he/she picks it up and connects it with the PIM, without touching the topside of the sterile drape.

Wireless communication in a robotical surgical system is known from US2008/0147089A1. A robotic surgical system comprises a carriage link of a robotic manipulator including a printed circuit assembly and a link communication device, positioning a sterile drape over the robotic manipulator, mounting a removable surgical instrument on the carriage link, and passing data wirelessly in either or both directions through the sterile drape between the link communication device and the surgical instrument along with power for electrical circuitry on the instrument.

SUMMARY OF THE INVENTION

There may thus be a need to provide a connection for sterile devices used during interventional procedures so that crossing the sterility barrier ensures the sterility of the procedure in a safe and simple manner.

The object of the present invention is solved by the subject-matter of the independent claims; further embodiments are incorporated in the dependent claims. It should be noted that the following described aspects of the invention apply also for the connector, for the connector system and for the method for connection through the flexible barrier.

According to the present invention a system for connecting an intravascular device and a further component through a flexible barrier is provided. The system comprises a connector having at least a device pad and at least a landing pad. The device pad is configured to be arranged in close proximity to the landing pad for establishing a contactless connection through the flexible barrier to transmit and/or receive data and/or power between the intravascular device and the further component. The device pad is configured to be connected to the intravascular device and the landing pad is configured to be connected to the further component. Further, the device pad and the landing pad are configured to attach and/or align to each other.

Accordingly, the present invention provides a different way of making the connection through the flexible barrier, in particular for making a connection across a sterility barrier, such a drape, between a sterile intravascular device and a non-sterile further system component. Thus, users can work above the drape and crossing the sterility barrier for connecting an intravascular device to a further system component in a non-sterile area is no longer a concern because a connection is established by attaching and/or aligning the device pad and landing pad across the sterility barrier, thus enabling the exchange of power and data across the barrier in a contactless manner.

The connector can be provided with different (active) devices such as intravascular ultrasound (IVUS) catheters, pressure wires, ultrasound probes, e.g. extravascular ultrasound (EVUS), atherectomy devices (based on laser, motor, etc.), hemodynamic measurements. Also, in some examples, user interfaces such as tools, buttons, wheels, etc. which are used in a cathlab, may be combined with a device pad of a specific device. This invention addresses the primary user challenge of connecting the device to the a further system component, such as a console, a patient interface module (PIM) and so forth, in a cathlab, while crossing the sterility barrier. At the same time, the proposed solution also addresses or at least supports the user need regarding the location of the tools and devices described above.

The connector provides a different way of making a connection between a device, e.g. a catheter, and a patient interface module (PIM), for example. The connection is made between a sterile device and a non-sterile PIM at a patient table. Between the sterile device and the non-sterile PIM or a non-sterile console, a flexible barrier is managed. The flexible barrier can be a drape comprising a plastic sheet or suitable textile. The flexible barrier can be transparent, partially or fully non-transparent.

In examples, the flexible barrier is optically transparent for electromagnetic radiation emitted from a light emitting diode (LED), a laser, infrared (IR) etc. In that example, exchanging data between the landing pad and device pad in a contactless manner may comprise receiving and transmitting of information encoded by means of visible or infrared light.

The flexible barrier is sterile on one side and non-sterile at the other side defining a sterile zone and a non-sterile zone. All electrical equipment in the sterile zone is crossing above the flexible barrier along with the associated cables.

The connector strongly facilitates user handling of the equipment, e.g. catheters etc., above the flexible barrier and crossing the sterile side of the flexible barrier is no longer a concern because power and data are crossing it in a contactless manner.

The connector comprises at least a device pad and at least a landing pad. The device pad can also be referred to as transmitter. The landing pad can also be referred to as receiver. The device pad and/or the landing pad is configured to transmit and/or receive data. Power transmission is provided from the landing pad to the device, e.g. a catheter, via the device pad. The device pad as well as the landing pad provide suitable electronics for the contactless transmission/reception of data and/or power. In examples, the pads are provided as encapsulated, preferable completely encapsulated casings or housings for both transmitting and receiving ends, thereby avoiding potential fluid or dust ingress. In examples the pads are made of suitable plastic material. Preferably, the transceiver on the catheter side (device pad) is 'passive' and cheap so the circuit can be integrated in a connector as part of a disposable.

The contactless connection is configured to exchange power and/or data between the device pad and the landing pad. The device pad is arranged in close proximity to the landing pad for the contactless connection through the flexible barrier. As will be described in more detail below, one or more device pads and/or one or more landing pads can be provided by the connector, so that different requirements or procedure settings can be provided.

In examples the landing pad or the lower part of the connector is positioned below the flexible barrier, i.e. at the non-sterile side of the flexible barrier, and the device pad or the upper part of the connector is positioned above the flexible barrier, i.e. at the sterile side of the flexible barrier.

In other words, the connector provides connection for one or more devices, e.g. the connection of one or more catheters to the console system, in a contactless fashion, where data and/or power is exchanged through the flexible barrier. The device pad (the transmitter) and the landing pad (receiver) are in contact with only the sterile barrier, e.g. drape, in between.

The transmit distance from the device pad to the landing pad is between 0.5 mm and 5 mm, preferably between 1 mm and 2.5 mm. This distance is determined by the thickness of the flexible barrier (which is determined by the materials used and may be as less as 0.1 mm), and the wall thickness of the housing or casing of the landing pad and device pad, which is typically between 0.5 and 2 mm.

A high data rate for a digital data stream or high bandwidth for an analog stream is provided over the contactless connection. The high data rate ranges from 100 Mbit/s up to a several Gbit/s, bandwidth ranges from 20 MHz up to 100 MHz (see also details below). The short distance as described above supports such data transmission, so that high data rate or bandwidth is achieved. For example, near-field data transmission and/or inductive power transmission techniques may be used.

The connector also enables a user, e.g. a physician, to temporarily disconnect and relocate the intravascular device, e.g. catheter, in the sterile field as the whole device is still sterile (no non-sterile parts are physically attached to the catheter). Furthermore, the device can be reconnected easily at a later stage to continue the procedure without worrying about crossing the sterile barrier.

The connector provides several advantages over the existing approach of the physical electrical connection. For example, a poke-yoke connection through the flexible barrier (sterility barrier) is provided. Interventions are performed faster, so that more patients per day can be treated. Also, intervention costs might decrease. Furthermore, there is a lower risk of sterility mistake which could increase a procedure length (e.g. physicians need to wash up again, new catheter to be opened); also no second catheter is needed (double costs are avoided). Cleaning of the relevant surfaces in-between procedures is made easier. There is a reduced risk of contrast fluid influencing the contactless contact between catheter and PIM. Furthermore, implicit generation of an electrical isolation barrier may be provided by the connector (means of patient protection).

According to an example, the device pad and/or the landing pad are configured to align to each other by aligning a shape thereof. The device pad and the landing pad can be aligned by their shape. Also a switch or a button can be provided to connect the pads. However, such connection remains easily removable or detachable prohibiting potential damage to either side of the connection e.g. in the event of equipment, a tool or a user accidently pulls a wire of the device with unintended excessive force, or in case of an emergency, where the devices are quickly disconnected for access with a defibrillator. In other words, the connection of the pads provides protection against unintended pull forces.

According to an example, the device pad and/or the landing pad are configured to attach and/or align to each other by tactile feedback. Such tactile feedback can be provided by magnetic elements provided at the pads. In some examples, vibration is provided as tactile feedback when the pads are correctly arranged in close proximity. In other examples a mechanical click may serve as a tactile feedback indicating the required arrangement of the pads.

According to an example, the device pad and/or the landing pad are configured to align and/or attach to each other via magnetic force. The pads at both sides of the flexible barrier are automatically aligned when the pads are in proximity to each other. Such auto-alignment can be provided by an electro-magnet to prevent issues with pacemakers and other devices that react to magnet fields. In examples, the electro-magnet can be activated via the system (e.g. software) and disabled with a hardware release button.

According to an example, the device pad and the landing pad are configured to align and/or attach to each other via a mechanical fixture. The mechanical fixture can be configured to fix the device pad to a recess or an extension of a casing or housing of the landing pad. A button, a latch or the like can be provided which extends from the device pad, e.g. sideways and/or in direction to the landing pad, and is received in the recess/extension of the landing pad, so that the pads are aligned and attached to each other. In examples, the button, latch or the like is released or pushed to extend from the device pad. The connection of the pads remains easily removable. The connection is provided with the flexible barrier arranged between the device pad and the landing pad.

The pads at both sides of the flexible barrier are automatically aligned when the pads are in proximity to each other. In examples, the device pad and the landing pad are configured to align and/or attach to each other via electrostatic elements.

According to an example, a further device pad is arranged adjacent to the device pad in close proximity to the landing pad and wherein the further device pad is configured to retransmit a received signal to the device pad. In examples, galvanic coupling is provided for data and/or power transmission between the pads. In examples, only one device pad is active at the same time. Whether a device pad is active is controlled through software linked to the landing pad. In examples, each device pad is modulated on a different frequency. The landing pad and the device pad each comprises electronic units.

In examples, the device pads can be stacked on top of each other on one single landing pad (with a single drape in between the landing pad and the first or closest device pad). Stacking the device pads provides improved usability particularly when space is scarce, so that the footprint is minimized. The landing pad is configured to transceive all modulated frequencies of the one or more device pads. The device pads comprise units for transceiving these signals multiplexed onto each other. Furthermore, an individual device pad is configured to filter out its own signal.

According to an example, a plurality of landing pads are arranged adjacent to each other. Multiple connections between device pads and landing pads are possible simultaneously by having multiple 'connection locations' in a lateral plane: the device pads are arranged adjacently, i.e. laterally in close proximity to the provided landing pads.

In examples, the landing pads are arranged in a lateral plane. The landing pads can be arranged singly, in a row or as an array. In examples, one or more landing pads are received in an enclosure. Optionally, at least one recess can be provided in the enclosure for receiving one or more landing pads.

In examples, the connector provides a combination of a single device pad and a single landing pad. In other examples, the connector comprises multiple device pads and a single receiver, wherein the single receiver is provided by multiple landing pads arranged laterally in a row or array and electrically connected to act as a single receiver. Accordingly, the multiple device pads are then placed next to each other at different lateral positions. Further examples provide a connector with multiple landing pads which are arranged independently, e.g. attached to a support structure (patient bed or patient support table) or integrated within the support structure (described in more detail below). In such examples, the device pad(s) can be switched from the location of one landing pad to the location of the next landing pad. In other examples, the connector comprises multiple device pads for a single landing pad, where the device pads are placed on top of each other.

Unique identification, e.g. via short-range radio-frequency identification (RFID) can be provided to identify the correct coupling between the device pad and the landing pad. Furthermore, such unique identification may serve for identifying which landing pads are active, i.e. are connected to a device pad in a contactless manner.

According to an example, one or a plurality of landing pads are configured to be attached to and/or integrated within a patient support structure or a device separated therefrom. A support structure can be a patient bed or a patient table. The device can for example be a cart, a mobile console, a patient interface module (PIM) or an intra venous (IV) pole. The landing pads are attached to or integrated within a bedrail, a frame or the patient table itself. Preferably the landing pads are attached or integrated at locations of the bedrail or frame, so that the cables of the devices/equipment is out of the way of the users. In examples, the one or more landing pads are attached to or integrated within the top of the patient support structure. The landing pads can be attached or integrated anywhere around the patient support structure. The according locations are, for example, a rail space or any other suitable location of the patient support structure. The rail space might be generally limited to the foot side of the bed up to half way the patients torso. In examples, the landing pads are attached or integrated within a device, such as a cart, a mobile console or an IV pole separated from the patient table. In examples the landing pad is provided with an enclosure which is attached to and/or integrated within a patient support structure or a device, as described before.

According to an example, the device pad is provided with a converter cable and/or converter dongle. The converter cable and/or provides the use of the connector with existing device connectors. Also, in case the device pad is provided as re-usable the converter cable and/or provides separation of the pad from the device. The converter dongle can be provided connecting the device pad with existing connectors ('legacy' connectors). The converter cable and/or converter dongle can also be re-usable and provided as sterilizable. Or they are provided as sterile for single use or one time use.

According to an example, transmission of power and/or data is provided by optical and/or electromagnetic transmission. The contactless power requirements are limited, since the devices typically consume up to 25 W power The contactless data link needs to be able to transceive significant amounts of data. Signals may be transferred digitally or analogue, depending on what is most convenient in terms of technology, cost, size, etc. An analogue bandwidth may include 35 MHz to 60 MHz. The according digital data rate is about 0.6 Gb/s for 35 MHz, about 2 Gb/s for 45 MHz and about 6 Gb/s for 60 MHz.

With respect to the transmission of data, only a very short distance (up to ~5 mm) needs to be covered. Therefore, the frequency (FM) modulation with sufficient modulation depth to achieve good (signal to noise) SNR signal transfer or other modulation schemes (QAM, FSK, . . . ) can be used. A 60 GHz carrier can be used in accordance to the IEEE802.11-ad standard. Also, optical radiation (e.g. light) may be used to transfer data (signal) (and/or power) by using fast modulation of a light source that penetrates through the flexible barrier, e.g. drape. Also sensitive photodiodes can be used for data (signal) and/or power transmission. This can be used for both opaque (blue, green) as well as transparent drapes (usually, opaque drapes have a transparent section at the edge).

With respect to the transmission of power, only a very short distance (up to ~5 mm) needs to be covered. Several ways of power transmission are possible: electromagnetic coupling such as inductive power transmission techniques. Alternatively or in addition, optical radiation (e.g. light, IR) may be used to transfer power (as well as data) through the flexible barrier using sensitive photodiodes to receive transmitted optical power.

In examples, shielding of signals is provided, e.g. contactless signals or power signals, by the Faraday cage principle such as a metal cage, for example. Shielding can be also provided by magnets or by using high frequency transmissions that are easily absorbed in air (e.g. 60 GHz). Also a combination of these shielding types is possible.

Improved use flow is achieved when using the inventive connector. The device pad(s) can be easily connected at the landing pad(s). The device pad(s) can be easily replaced from one landing pad to the next in case multiple landing pads are provided.

According to the present invention, also a system for connection through a flexible barrier is provided. The system comprises at least a connector and at least an interventional device, wherein the connector comprises a connecting side of the interventional device, and wherein a device pad of the connector is arranged in close proximity to a landing pad of the connector for contactless connection through the flexible barrier.

According to an example, the system further comprises a patient support structure, wherein the connector is attached or integrated within the patient support structure.

According to the present invention, also a method for connection through a flexible barrier is provided. The method comprising the following steps: a) connecting at least a device pad of a connector to an intravascular device; b) connecting at least a landing pad of the connector to a further component; c) arranging the device pad in close proximity to the landing pad for contactless connection through the flexible barrier; d) establishing a contactless connection between the device pad and the landing pad; wherein the device pad and/or the landing pad is configured to transmit and/or receive data and/or power and wherein the contactless connection is configured to exchange power and/or data between the device pad and the landing pad.

According to the present invention, also a computer program element for controlling an apparatus, i.e. the connector or the system is provided, which, when being executed by a processing unit, is adapted to perform the method steps. Also, a computer readable medium is provided having stored the program element.

In other words, the invention proposes to connect a device, e.g. a catheter to a console system or other systems in a cathlab in a contactless fashion, where data & power is exchanged through a flexible barrier, e.g. a drape, whereby the transmitter (device pad) and receiver (landing pad) are in close contact with only the sterile barrier (drape) in between, as illustrated in the Figures. Although the principle of signal and power transfer is known (e.g. contactless charging of mobile phones), it is a unique feature of this invention to cross the sterility barrier, physically consisting e.g. of the drape that is stacked between receiver and transmitter.

Multiple connections are envisaged simultaneously by having multiple connection locations adjacent to each other, or by stacking the connector pads, i.e. the device pads, on top of each other on one single landing pad, with a single flexible barrier, e.g. the drape, in-between the landing pad and first device pad of the connector. Alignment of landing pad and device pad may be assured for example by: shape determined fit; auto-alignment through magnets that keep the pads at both sides of the drape aligned with respect to each other; electro-magnet to prevent issues with pacemakers and other devices that react to magnet fields, wherein the electro-magnet can be activated via the system (e.g. software) and/or disabled with a hardware release button.

The described features of the invention also apply to applications, wherever signal and/or power needs to be transferred across a sterile barrier (where the barrier consist of a physical sheet, such as the drape for example). Such applications comprise hemodynamic measurements, e.g. dynamic monitoring in operating rooms, patient monitoring, 2D or 3D ultrasound, used to determine access location to a vein or artery. Using the proposed contactless data and power connection to cross the flexible barrier allows to show on the large interventional display in the patient room without hassle. Power and data to other devices that need to cross the sterility barrier is provided.

Although the connection of the device pad and the landing pad is described through the flexible barrier (sterility drape) omitting the drape would not limit the function of the contactless power & data interface.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list. The drawings shown in the figures are not drawn to scale.

IGT devices solution for coronary or peripheral interventions in cathlabs works with catheters, wires or other interventional devices inserted into arteries of the human body and pushed to the proper location in the human body by the physician. The clinical context for the use of the catheters wires and other interventional devices is that those parts of the body suffer from limited oxygenation due to limited blood flow. This could be the heart, but also limbs or organs. The limited blood flow is caused by local narrowing of the blood vessel ('stenosis') and diagnosis and treatment aims at identification and removal of the stenosis. Classic diagnosis and treatment is done under X-ray, but can be limited due to the 3D nature of the problem in combination with 2D imaging. Furthermore, a contrast agent must be added to the blood stream to visualize vessels, which can be harmful to the patient. In addition, the general trend is to minimize the applied X-ray dose for the health of both the patient and the physician.

Therefore, the mentioned devices must be sterile throughout the whole procedure. In a cathlab there are fixed/integrated systems and also 'mobile' cart-based systems for data acquisition and power provision during the procedures. The fixed systems are usually provided with cables mounted below the floor of the cathlab and connected to a frame of a patient support table. On the other hand, the mobile systems have rather a direct connection to the patient bed.

Thus all devices and tools which are used must be sterile through the whole procedure. User requirements in the cathlab in relation to the devices and tools are basically: (i) being able to work above the sterile side of the drape without the need to reach below the non-sterile side of the drape, (ii) having the tools where the user needs them, which could also include a change of the location, and (iii) having those tools ready when the users are ready to use them, without the need of tool exchange due to non-sterile contact or the like, for example.

The present invention provides a connector, a system and a method which meets the needed requirements and facilitates the use of interventional devices by making the connection through the flexible barrier. The result is, that the users can work above the drape and crossing of the sterility barrier is no longer of concern because power and data are crossing the flexible barrier in a contactless manner. The different connectors described below provide all the features described above.

Figure 1:
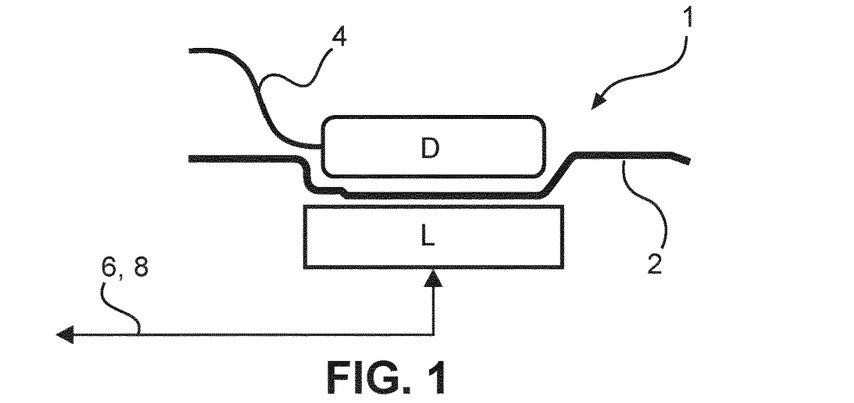
FIG. 1 schematic drawing of a connector comprising a device pad and a landing pad.

FIG. 1 shows a schematic drawing of a connector 1 comprising a device pad D and a landing pad L. A flexible barrier 2 is shown between the device pad D and the landing pad L. The flexible barrier 2 is a drape which is sterile on one side and non-sterile on the other side. However, in examples, the connection can also be established without the flexible barrier 2 between the pads D, L. The landing pad L is located below a flexible barrier 2, i.e. at the non-sterile side. The device pad is located above the flexible barrier 2.

The device pad D is provided with a cable of a device or tool. The pads D, L are configured to transmit and/or receive data 8 and/or power 6. Power 6 and data 8 are exchanged via a contactless connection which is described in more detail in FIG. 2. For establishing the contactless connection, the device pad D and the landing pad L are arranged in close proximity. The distance between the device pad D and the landing pad L is as described above.

The pads D, L are configured to be aligned to each other when in close proximity, so that a contactless connection is established between the pads D, L. If a flexible barrier 2 is provided the contactless connection is established through the flexible barrier 2. Power transmission is provided in a contactless manner from the landing pad L to the intravascular device which is used, e.g. a catheter, via the device pad D and the cable 4 of the device. Data transmission is provided in a contactless manner both ways from/to the landing pad L and the device pad D. In examples, the pads D, L are provided as encapsulated, preferable completely encapsulated casings so that potential fluid or dust ingress is avoided. The pads D, L are made of suitable plastic material or other suitable material.

Although described for a connector having a single landing pad L and a single device pad D the described features also apply for connecters with more device pads D and/or landing pads L.

Figure 2:
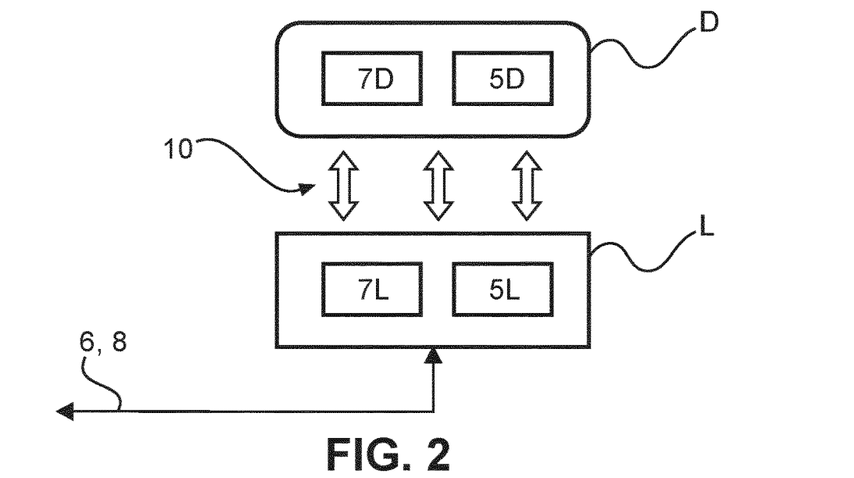
FIG. 2 enlarged view of the connector of FIG. 1 showing a contactless connection.

FIG. 2 shows an enlarged view of the connector of FIG. 1 showing the contactless connection established between the device pad D and the landing pad L. The device pad as well as the landing pad provide suitable electronics for the contactless transmission/reception of data 8 and/or power 6.

The device pad D comprises electronical units 5D, 7D for contactlessly receiving and transmitting power 6 and data 8. The landing pad L also comprises electronical units 5L, 7L for contactlessly receiving and transmitting power 6 and data 8. In other words, one or more units 5D, 5L for contactless transmission of the data signal (where data can be analog and digital) as well as one or more units 7D, 7L for contactless transmission of power are provided. In embodiments, the units 5D, 5L, 7D, 7L may comprise control signals, data storage units such as buffer or memory, and microcontroller. The microcontroller can be configured to generate control signals for each pad to make sure the units operate as intended.

Furthermore, the landing pad L has also a power unit 5L for providing the needed power for the according device which is associated with the device pad D.

The contactless connection 10 is established between the device pad D and the landing pad L. The details of power and data transmission via the contactless connection is as described above.

The alignment and/or attachment of the pads D, L will become more apparent as described with reference to the following figures. In some figures, the elements of the connector 1 are shown further apart, for providing a better understanding.

Figure 3:
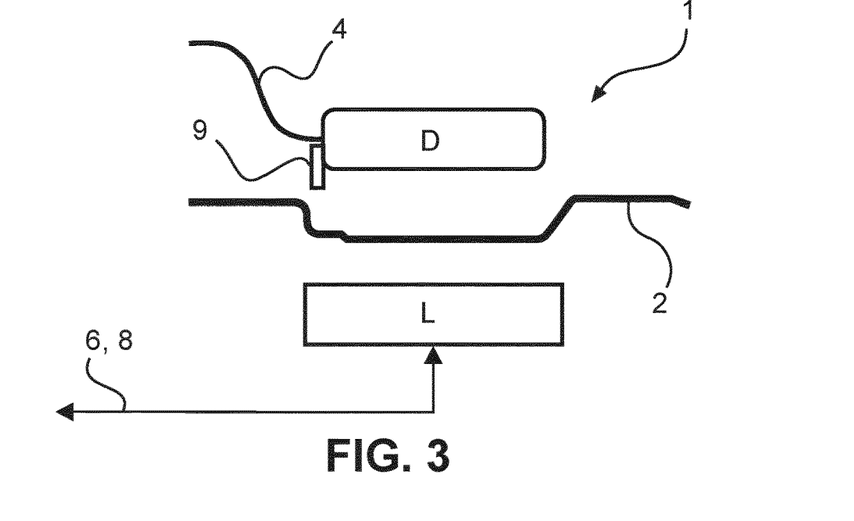
FIG. 3 schematic drawing of a connector providing shape alignment for the device pad and landing pad.

FIG. 3 shows a schematic drawing of a connector 1 providing shape alignment for the device pad D and landing pad L. For example, a switch 9 (shown schematically) can be provided which connects the pads D, L in a loose manner providing potential mechanical detachment. In other embodiments a button can be provided instead of the switch 9 for attachment/detachment of the pads D, L.

Figure 4:
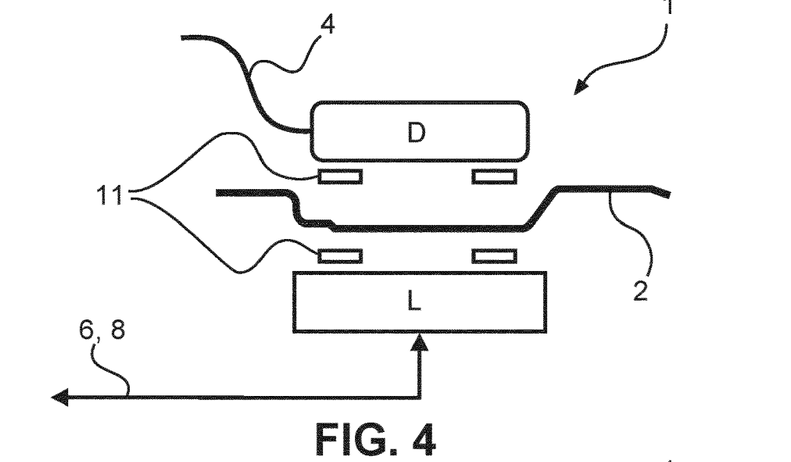
FIG. 4 schematic drawing of a connector providing tactile feedback for alignment and/or attachment of the device pad and landing pad.

FIG. 4 shows a schematic drawing of a connector 1 providing tactile feedback for alignment and/or attachment of the device pad D and landing pad L. The device pad D and the landing pad L are provided with magnetic elements 11 attracting the pads D, L to each other, so that correct alignment and detachment is achieved. In some embodiments electromagnetic elements 11 are used, so that the pads D, L are aligned and attached in an automatic or semiautomatic manner. The electromagnetic elements 11 also prevent issues with pacemakers and other devices that react to magnet fields.

Figure 5:
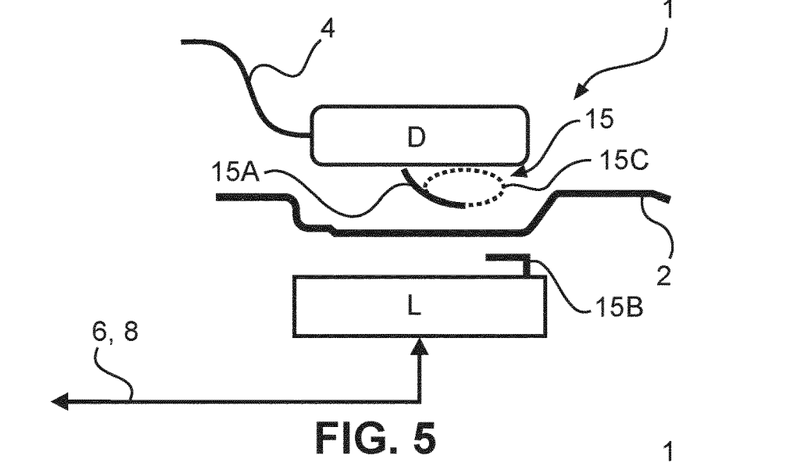
FIG. 5 schematic drawings of a connector providing mechanical fixture for the connection of the device pad and landing pad.

FIG. 5 shows a schematic drawings of a connector 1 providing a mechanical fixture 15 for the connection of the device pad D and the landing pad L. The flexible barrier 2, e.g. a drape, is arranged between the pads D, L.

The mechanical fixture 15 comprises an extension 15B of the landing pad receiving the latch 15A of the device pad. The latch 15A is made of flexible plastic, for example, so that it deforms or bends when pushed into the bended extension 15B. The latch 15A is then fixedly received within the extension 15B. When receiving the latch 15A also the flexible barrier 2 is received by the extension 15B (the flexible barrier 2 covers the latch 15A inside the extension 15B.

In embodiments, the latch 15A is provided with a round shape 15C (shown as dotted line) at its end, so that the round shape 15C deforms when pushed in the extension 15B. Instead of a latch also a suitable button or the like can be provided which extends from the device pad D, e.g. sideways or in direction to the landing pad, and is received in an accordingly shaped recess or extension, so that the pads D, L are aligned and attached to each other. In the embodiments, the connection of the pads D, L remains easily removable.

In other embodiments electrostatic elements are provided instead of magnetic elements 11. In other embodiments, vibrational elements or a mechanical click can be used instead of the magnetic elements 11, so that a vibrational feedback is provided when the pads D, L are arranged correctly.

In further embodiments, feedback can be provided on how the device pad and landing pad can be correctly or optimally aligned and/or arranged with respect to each other. This may, for example, be beneficial in case when the landing pad is not visible to a user, for example when it is located below a non-transparent surgical drape forming the sterility barrier.

For example, visual feedback may be provided by means of light emitting diodes (LEDs) indicating where the connection may be established. For example, one or more LEDs can be provided at the periphery of the landing pad. In an example, LEDs may be placed along the length of an outline pf the landing pad. In case multi-coloured LEDs are used, different colours of lighting may indicate either optimal or non-optimal alignment of the device pad and the landing pad. For example, green lighting may indicate an optimal alignment while yellow lighting may indicate a non-optimal alignment.

Alternatively or in addition, user feedback may be provided as audible or haptic feedback. For example, when a device pad is placed on the landing pad, it may be attracted to the surface in a preferred location for an optimal connection by means of an (electro) magnetic force. Alternatively, the user can experience vibrations in the device pad through his hands.

Figure 6:
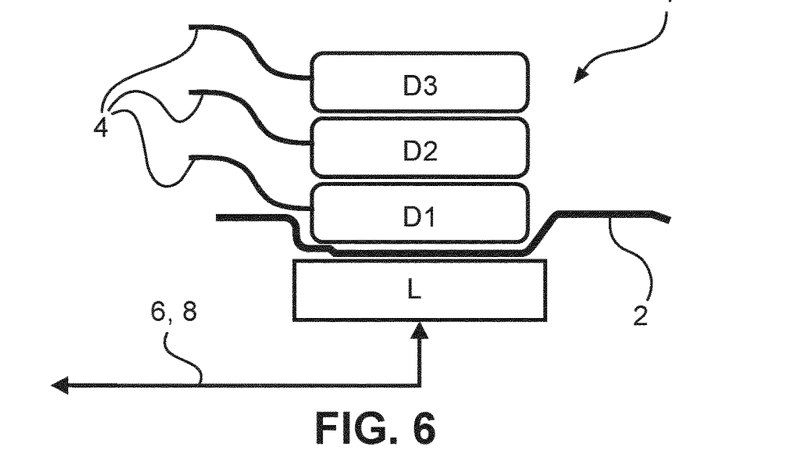
FIG. 6 schematic drawing of a connector, wherein the device pads are arranged on top of each other.

FIG. 6 shows a schematic drawing of a connector 1, wherein the device pads D1, D2, D3 are arranged on top of each other. A single landing pad L is provided in this embodiment. The device pads D1, D2, D3 are arranged adjacent to each other in a stacked manner. Each device pad D is provided with a cable 4 of a device or tool.

A flexible barrier 2 is provided in between the landing pad L and the first device pad D1. The remaining device pads D2, D3 are arranged on top of the first device pad D1. The device pads D1, D2, D3 are provided with suitable elements for establishing the data 8 and power 6 transfer between the landing pad L and the according device pad D. For the alignment and attachment of the multiple device pads D1, D2, D3 the same applies as for the alignment and attachment of the device pad to the landing pad (see description above and the according figures).

Each device pads D1, D2, D3 is configured to retransmit the received signal, e.g. the received data, from top to bottom. For example, the signal is received by device pad D3 and transmitted to device pad D2 and then to device pad D1. Similarly, if the signal is received by device pad D2 it is transmitted to device pad D1. The signal is received by the landing pad L from closest device pad D1.

Figure 16:
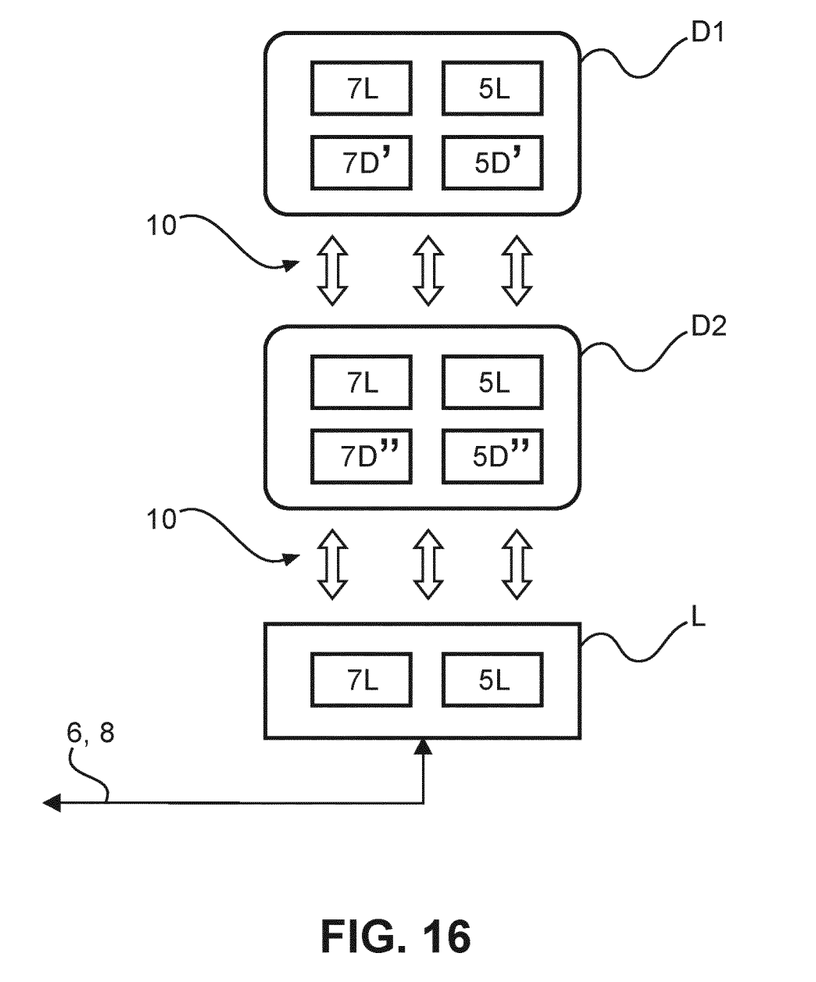
FIG. 16 schematic drawing of a connector, showing contactless connection of device pads are arranged on top of each other.

If re-transmission of data is required for the stacked device pads D1, D2, D3, relevant units (see also description of FIG. 2) are provided FIG. 16 shows a schematic drawing of a connector 1. Contactless connection through the flexible barrier is established for two device pads D1, D2 arranged on top of each other in close proximity to the landing pad L. The details of power and data transmission via the contactless connection is as described above. The flexible barrier 2 is arranged between the landing pad L and the closest device pad D2 (not shown in FIG. 16).

The device pads D1, D2 comprise electronical units 5D', 7D', 5D", 7D" for receiving and transmitting power 6 and data 8 in a contactless manner. The landing pad L also comprises electronical units 5L, 7L for receiving and transmitting power 6 and data 8 in a contactless manner. As described in FIG. 2 one or more units 5D', 5D", 5L for contactless transmission of the data signal (where data can be analog and digital) as well as one or more units 7D', 7D", 7L for contactless transmission of power are provided.) In embodiments, the units 5D', 5D", 5L, 7D', 7D", 7L may comprise control signals, data storage units such as buffer or memory, and microcontroller. The microcontroller can be configured to generate control signals for each pad D1, D2 to ensure the units operate as intended. In embodiments multiple device pads are arranged adjacent to each other.

One of the device pads D1, D2 is active at the same time. Whether the device pad D1 or device pad D2 is active is controlled through software linked to the landing pad L. In examples, each device pad D1, D2 is modulated on a different frequency.

The landing pad L is configured to transceive all modulated frequencies of the device pads D1, D2. The device pads D1, D2 comprise units 7L, 5L for transceiving these signals multiplexed onto each other. The device pads D1, D2 are configured to filter out their own signal.

Stacking the device pads D1, D2, D3 provides improved usability particularly when space is scarce, so that the footprint is minimized.

Figure 7A:
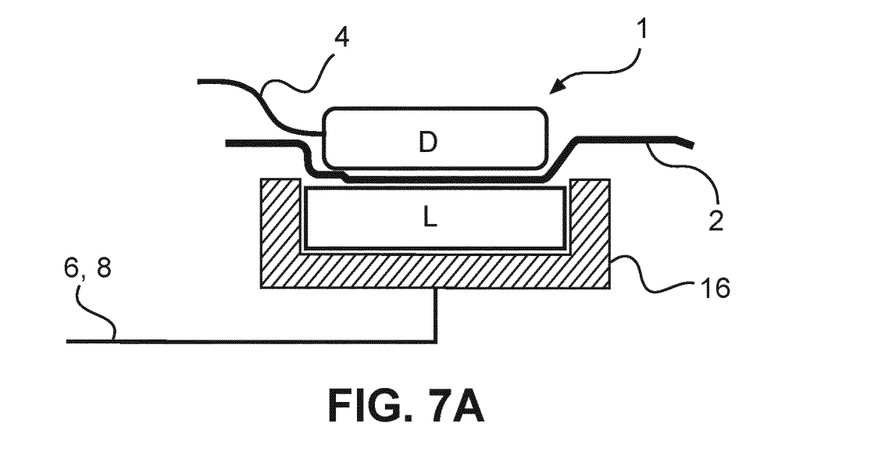
FIG. 7A schematic drawing of a connector, wherein the landing pad is received in an enclosure.

FIG. 7A shows a schematic drawing of a connector 1, wherein the landing pad L is received in an enclosure 16. The connector 1 is as described in FIG. 1 and in addition, the enclosure 16 provides electrical connections for data 8 and/or power 6 transfer to/from the landing pad L. The enclosure 16 can also serve for the alignment of the device pad D to the landing pad L according to their shape. Furthermore, the enclosure can be provided with elements, as described with reference to the other figures, so that alignment of the pads D, L by tactile feedback, magnets or electrostatic elements is also provided.

Figure 7B:
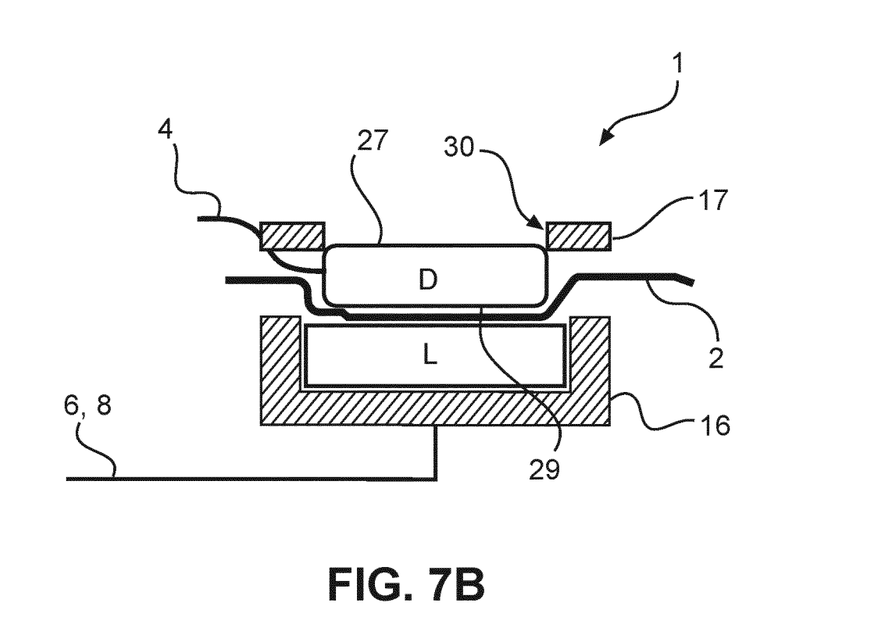
FIG. 7B schematic drawing of a connector, wherein the landing pad and the device pad is received in an enclosure.

FIG. 7B shows a schematic drawing of a connector 1, wherein the landing pad L and the device pad D is received in an enclosure 16, 17. The enclosure 17 of the device pad is similar to the enclosure 16 of the landing pad. The enclosure 17 can be provided as ring-shaped, so that the lower part 29 of the device pad D is extending outside the enclosure 17. In embodiments the enclosure 17 can be the same as the enclosure 16 for the landing pad L. The enclosure 17 extends above the top side 27 of the device pad D providing a recess 30 for a further device pad which is placed adjacent the device pad D. This is described in more detail in FIG. 8B.

Figure 8A:
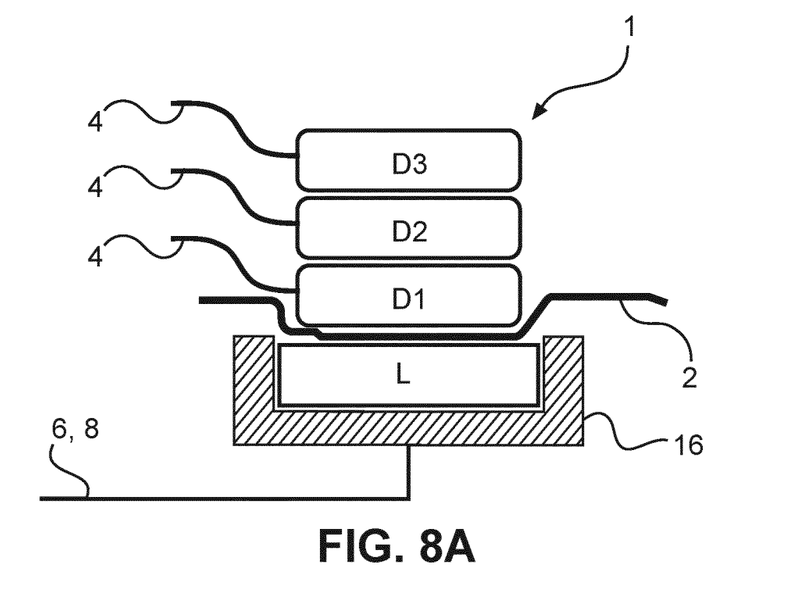
FIG. 8A schematic drawing of the connector of FIG. 7A, wherein multiple device pads are arranged on top of each other.

FIG. 8A shows a schematic drawing of the connector 1 of FIG. 7A, wherein multiple device pads D1, D2, D3 are arranged in a stacked manner, see also FIG. 6 for details. The landing pad L is received in an enclosure 16, as described in FIG. 7A.

Figure 8B:
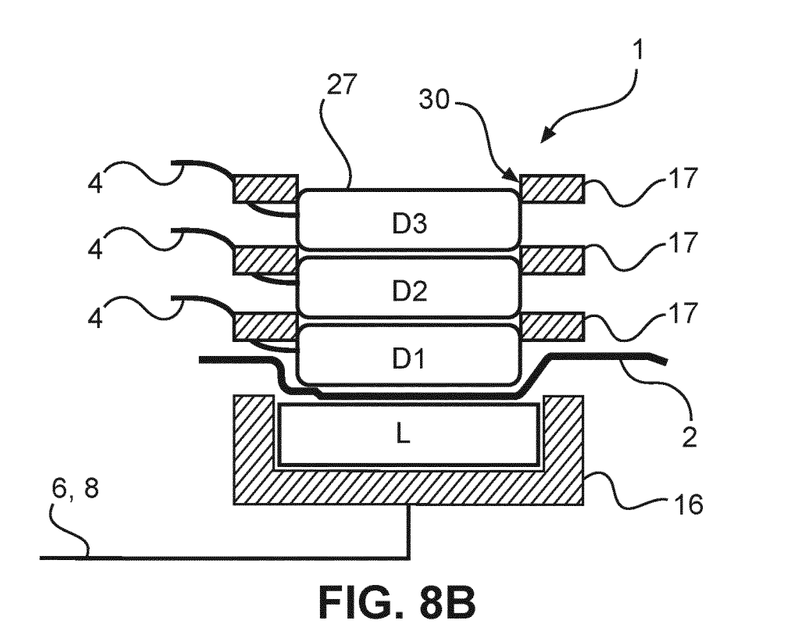
FIG. 8B schematic drawing of the connector of FIG. 8A, wherein each device pad is received in an enclosure.

FIG. 8B shows a schematic drawing of the connector of FIG. 8A, wherein each device pad D1, D2, D3 is received in an enclosure 17. The enclosure 17 for the device pad 17 is as described in FIG. 7B.

The top side 27 of each device pad D1, D2, D3 facing the above lying device pad D2, D3 provides an enclosure 17 having a recess 30 for receiving the above lying device pad. The alignment and attachment of the device pads D1, D2, D3 can thus be provided, wherein the closest device pad D1 is received in the enclosure 16 of the landing pad.

Figure 9:
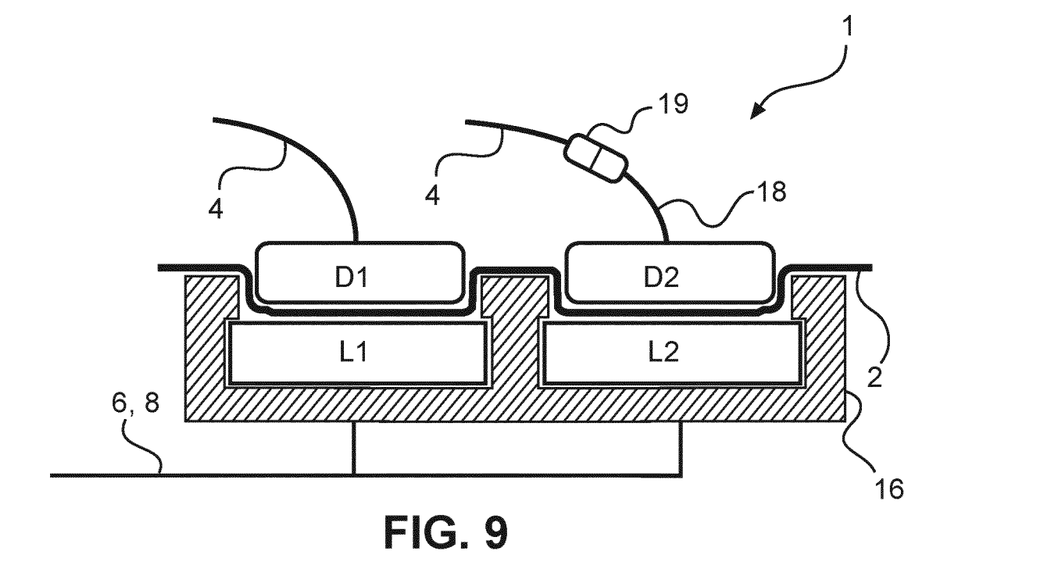
FIG. 9 schematic drawing of a connector, wherein two device pads are arranged adjacent to each other.

FIG. 9 shows a schematic drawing of a connector 1, wherein two device pads D1, D2 are arranged adjacent to each other. Two landing pads L1, L2 are provided in an enclosure 16. As described with reference to the figures above, a flexible barrier 2 is provided between the landing pads L1, L2 and the device pads D1, D2. The enclosure 16 is as described before.

Arranging the landing pads L1, L2 adjacent to each other provides multiple connections in a lateral plane. The device pads D1, D2 can be easily placed and removed for establishing a contactless connection as described in FIG. 2.

The landing pads L1, L2 are connected, providing a combined power 6 and data 8 connection from/to the enclosure 16. Within the enclosure, the landing pads L1, L2 are connected electronically in an appropriate manner to the enclosure 16 for data readout and/or power transfer.

One of the device pads D2 is provided with a converter cable 18. The converter cable 18 provides a connection with a device connector 19. The device connector 19 can be that of a catheter or any other tool used during the procedure. The converter cable 18 converts the connector 1 (providing the contactless connection through the flexible barrier 2) with the device connector 19.

In embodiments a converter dongle can be used having the functionality of the connector 1 and the device connector 19. The difference between the converter cable 18 and the converter dongle is that the dongle does not have a cable in between both connectors (connector 1 and device connector 19).

The converter cable 18 and converter dongle can be provided as sterile in case they are provided for single use or one time use. In case of multiple use they can be provided as sterilizable.

Figure 10:
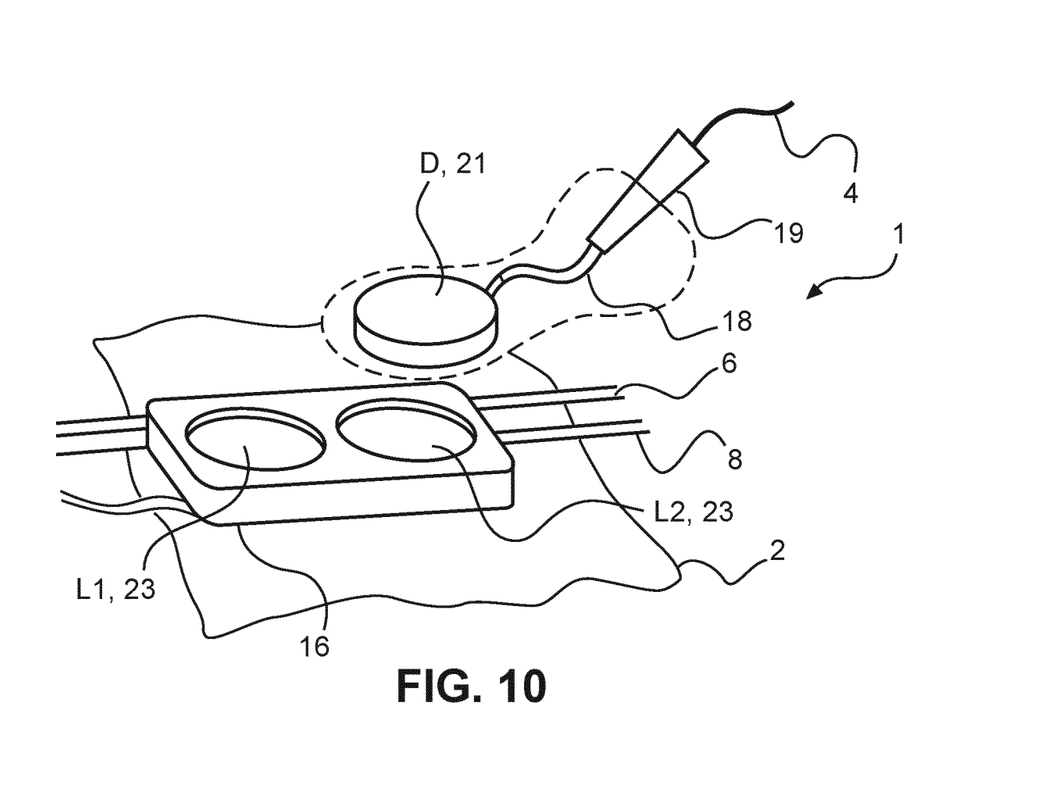
FIG. 10 perspective view of the connector of FIG. 9.

FIG. 10 shows a perspective view of the connector 1 of FIG. 9. In this embodiment the device pad D is provided with a disc-shaped casing 21 and the landing pads D1, D2 are also provided with a disc-shaped casing 23. In other embodiments different shapes of the casing are possible.

The converter cable 18 is encircled with a dash-line for improved understanding. In embodiments the converter cable 18 is replaced by a converter dongle (see also description of FIG. 9).

Figure 11:
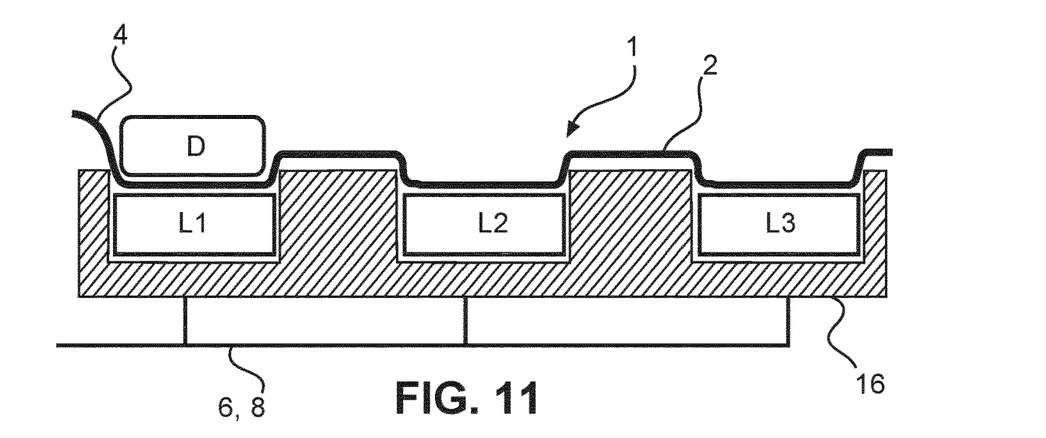
FIG. 11 schematic drawing of another connector example.
Figure 12:
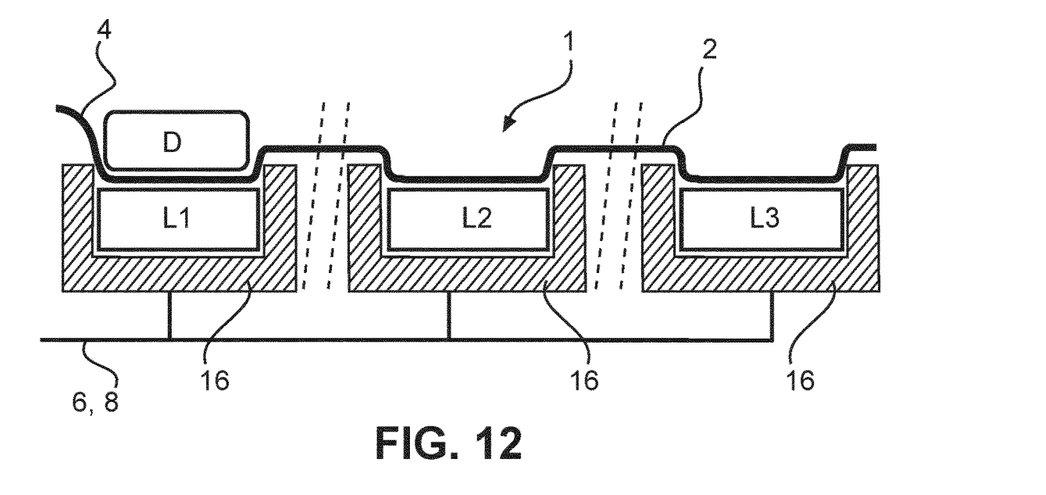
FIG. 12 schematic drawing of a further connector example.

FIG. 11 and FIG. 12 shows schematic drawings of another embodiment of a connector 1. For improved understanding only one device pad D is shown. However, multiple device pads D can be arranged adjacent or on top of each other, as described above. In FIG. 11 three landing pads L1, L2, L3 are provided in an enclosure 16. The landing pads L1, L2, L3 are arranged adjacent to each other. In other embodiments multiple landing pads L can be arranged within one enclosure 16.

In FIG. 12 each landing pad L1, L2, L3 is provided in a single enclosure 16. Such connector 1 provides the possibility to arrange the single landing pads L1, L2, L3 in their respective enclosures 16 in a variety of locations. The enclosures 16 are connected to a single data/power 6, 8 transmission. The enclosure 16 of FIGS. 11, 12 is as described before with reference to the other figures.

Figure 13:
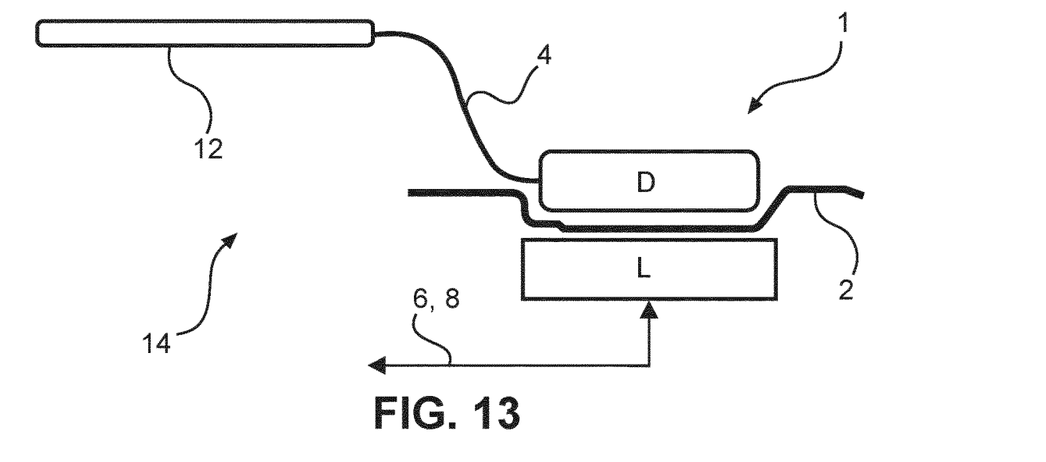
FIG. 13 schematic drawing of a system comprising an interventional device.

FIG. 13 shows a schematic drawing of a system 14 comprising an interventional device 12 and a connector 1. A connecting side, i.e. cable 4, of the interventional device 12 is connected with the device pad D. A contactless connection is established between the device pad D and the landing pad L, which are arranged in close proximity, so that power 6 and data 8 to/from the device 12 are transferred in a contactless manner. The flexible barrier 2 is provided between the device pad D and the landing pad L, so that the contactless connection is provided through the flexible barrier 2.

Figure 14:
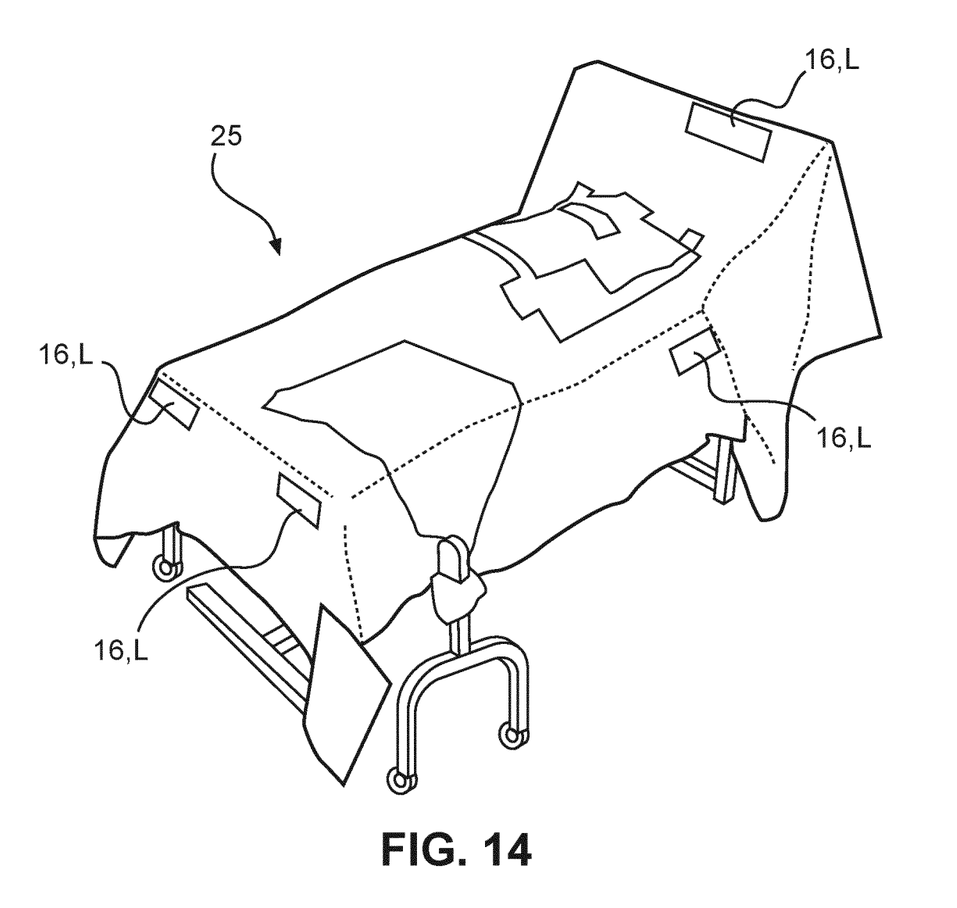
FIG. 14 schematic drawing of a patient support structure providing a plurality of landing pads.

FIG. 14 shows a schematic drawing of a patient support structure 25 providing a plurality of landing pads L. The landing pads L are provided as single landing pads L or arranged adjacent to each other in an enclosure 16 (the enclosures 16 and landing pads L are shown schematically). The patient support structure 25 is a patient bed, for example.

The landing pads L are provided at the top or head end of the patient support structure 25, at the foot end or at the sides. The landing pads L/enclosures 16 can be attached or integrated within a bedrail of the patient bed or support structure 25. Also, the landing pads L/enclosures 16 can be integrated within the support structure 25.

Interventional devices 12 or tools can be provided with a device pad D at their connecting end, so that the device pad D is arranged in close proximity to the landing pad L, as described above, so that power 6 and data 8 is transferred in a contactless manner.

Figure 15:
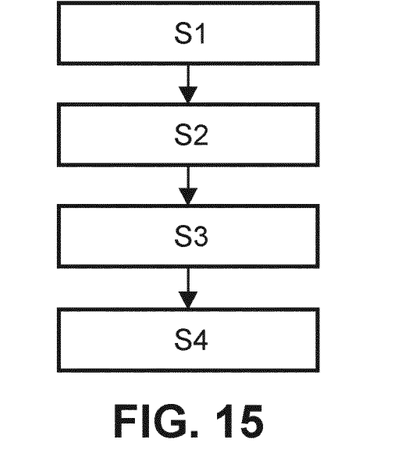
FIG. 15 flow chart of a method for connection through a flexible barrier.

FIG. 15 flow chart of a method for connection through a flexible barrier. At least a device pad D of a connector 1 is provided (step S1) and connected to an intravascular device 12. The device pad(s) D can be provided at the connecting side of the device 12 such as a catheter, tool, wheel etc. as used in a cathlab. At least a landing pad L of the connector 1 is provided (step S2). The landing pad(s) L can be provided attached or integrated in a patient support structure 25 or other structure in a cathlab, for example. The landing pad L is for example connected to a console or patient interface module PIM. The device pad(s) D is arranged (step S3) in close proximity to the landing pad(s) L for establishing (step S4) a contactless connection 10 through the flexible barrier 2.

The device pad(s) D and the landing pad(s) L is configured to transmit and/or receive data 8 and/or power 6, as described in more detail above. The contactless connection 10 is configured to exchange power 6 and/or data 8 between the device pad(s) D and the landing pad(s) L.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or contactless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for connecting an intravascular device and a further component through a flexible barrier, comprising:
 the intravascular device, and
 a connector having at least a device pad and at least a landing pad;
 wherein the device pad is configured to be arranged in close proximity to the landing pad for establishing a contactless connection through the flexible barrier to transmit and/or receive data and/or power between the intravascular device and the further component,
 wherein the device pad is configured to be connected to the intravascular device and the landing pad is configured to be connected to the further component, and
 wherein the device pad and the landing pad are configured to attach and/or align to each other.

2. System according to claim 1, wherein the device pad and/or the landing pad are configured to align to each other by aligning a shape thereof.

3. System according to claim 1, wherein the device pad and/or the landing pad are configured to attach and/or align to each other by tactile feedback.

4. System according to claim 1, wherein the device pad and/or the landing pad are configured to align and/or attach to each other via magnetic force.

5. System according to claim 1, wherein the device pad and the landing pad are configured to align and/or attach to each other via a mechanical fixture.

6. System according to claim 1, wherein a further device pad is arranged adjacent to the device pad in close proximity to the landing pad and wherein the further device pad is configured to retransmit a received signal to the device pad.

7. System according to claim 1, wherein a plurality of landing pads are arranged adjacent to each other.

8. System according to claim 1, wherein one or a plurality of landing pads are configured to be attached to and/or integrated within a patient support structure or a device separated therefrom.

9. System according to claim 1, wherein the device pad is provided with a converter cable and/or converter dongle.

10. System according to claim 1, wherein transmission of power and/or data is provided by optical and/or electromagnetic transmission.

11. System according to claim 1, wherein the further component of the system is a console or a patient interface module (PIM).

12. System according to claim 11, further comprising a patient support structure, wherein the connector is attached or integrated within the patient support structure.

13. A method for connection through a flexible barrier, comprising the following steps:
   a) connecting at least a device pad of a connector to an intravascular device;
   b) connecting at least a landing pad of the connector to a further component;
   c) arranging the device pad in close proximity to the landing pad for contactless connection through the flexible barrier;
   d) establishing a contactless connection between the device pad and the landing pad;
   wherein the device pad and/or the landing pad is configured to transmit and/or receive data and/or power; and
   wherein the contactless connection is configured to exchange power and/or data between the device pad and the landing pad.

14. The method according to claim 13, wherein arranging the device pad in close proximity to the landing pad comprises aligning the device pad and/or the landing pad by aligning a shape thereof.

15. The method according to claim 13, wherein arranging the device pad in close proximity to the landing pad comprises aligning the device pad and/or the landing pad with each other by tactile feedback.

16. The method according to claim 13, wherein arranging the device pad in close proximity to the landing pad comprises aligning and/or attaching the device pad and/or the landing pad to each other via magnetic force.

17. The method according to claim 13, wherein arranging the device pad in close proximity to the landing pad comprises aligning and/or attaching the device pad and the landing pad to each other via a mechanical fixture.

18. The method according to claim 13, wherein the method further comprises retransmitting, by a further device pad arranged adjacent to the device pad in close proximity to the landing pad, a received signal to the device pad.

19. The method according to claim 13, wherein transmission of power and/or data is provided by optical and/or electromagnetic transmission.

20. The method according to claim 13, wherein the further component of the system is a console or a patient interface module (PIM).

\* \* \* \* \*